United States Patent
Parviz et al.

(10) Patent No.: US 9,402,582 B1
(45) Date of Patent: Aug. 2, 2016

(54) SMART SURGICAL GLOVE

(71) Applicant: Verily Life Sciences LLC, Mountain View, CA (US)

(72) Inventors: Babak Parviz, Los Altos, CA (US); Chia-Jean Wang, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 76 days.

(21) Appl. No.: 14/257,823

(22) Filed: Apr. 21, 2014

(51) Int. Cl.
- *A61B 5/1455* (2006.01)
- *A61B 5/00* (2006.01)
- *A61B 5/145* (2006.01)
- *A61K 49/00* (2006.01)

(52) U.S. Cl.
CPC .......... *A61B 5/6806* (2013.01); *A61B 5/0013* (2013.01); *A61B 5/1455* (2013.01); *A61B 5/14546* (2013.01); *A61B 5/742* (2013.01); *A61B 5/7455* (2013.01); *A61K 49/0017* (2013.01)

(58) Field of Classification Search
CPC .. A61B 5/0059; A61B 5/0071; A61B 5/1455; A61B 5/6806; A61B 5/6825; A61B 5/6826; A61B 5/6838
See application file for complete search history.

(56) References Cited

U.S. PATENT DOCUMENTS

| | | | | |
|---|---|---|---|---|
| 5,079,629 A * | 1/1992 | Oz | ............... | A61B 5/6838 348/216.1 |
| 6,248,064 B1 * | 6/2001 | Gopinathan | ......... | A61B 5/6806 600/300 |
| 6,487,439 B1 * | 11/2002 | Skladnev | ............. | A61B 5/6806 600/310 |
| 6,589,171 B2 * | 7/2003 | Keirsbilck | ........... | A61B 5/6806 600/323 |
| 7,899,515 B2 | 3/2011 | Hashimshony et al. | | |
| 8,282,653 B2 | 10/2012 | Nelson et al. | | |
| 8,411,034 B2 | 4/2013 | Boillot et al. | | |
| 8,613,230 B2 | 12/2013 | Blumenkranz et al. | | |
| 2008/0171311 A1 * | 7/2008 | Centen | ................. | G09B 23/288 434/265 |
| 2010/0210924 A1 * | 8/2010 | Parthasarathy | ...... | A61B 5/6838 600/323 |
| 2011/0028860 A1 | 2/2011 | Chenaux et al. | | |
| 2013/0333094 A1 | 12/2013 | Rogers et al. | | |

OTHER PUBLICATIONS

Takats et al., "Identifying the margin: a new method to distinguish between cancerous and noncancerous tissue during surgery", Future Oncology, 2012, pp. 113-116.

* cited by examiner

*Primary Examiner* — Eric Winakur
(74) *Attorney, Agent, or Firm* — McDonnell Boehnen Hulbert & Berghoff LLP

(57) ABSTRACT

A smart surgical glove is provided that includes sensors configured to detect one or more properties of a target tissue and indicators configured to indicate the detected one or more properties of the target tissue. In some embodiments, the indicators are configured to provide a sensation to a wearer of the smart surgical glove that is related to the detected one or more properties of the target tissue. In some embodiments, the indicators are configured to transmit a signal to another device, for example, a head-mounted display worn by the wearer of the smart surgical glove. In some embodiments, the smart surgical glove is configure to illuminate a fluorescent imaging agent in the target tissue and to detect one or more properties of the target tissue related to the presence of the imaging agent. Additionally included are methods of using such smart surgical gloves.

19 Claims, 6 Drawing Sheets

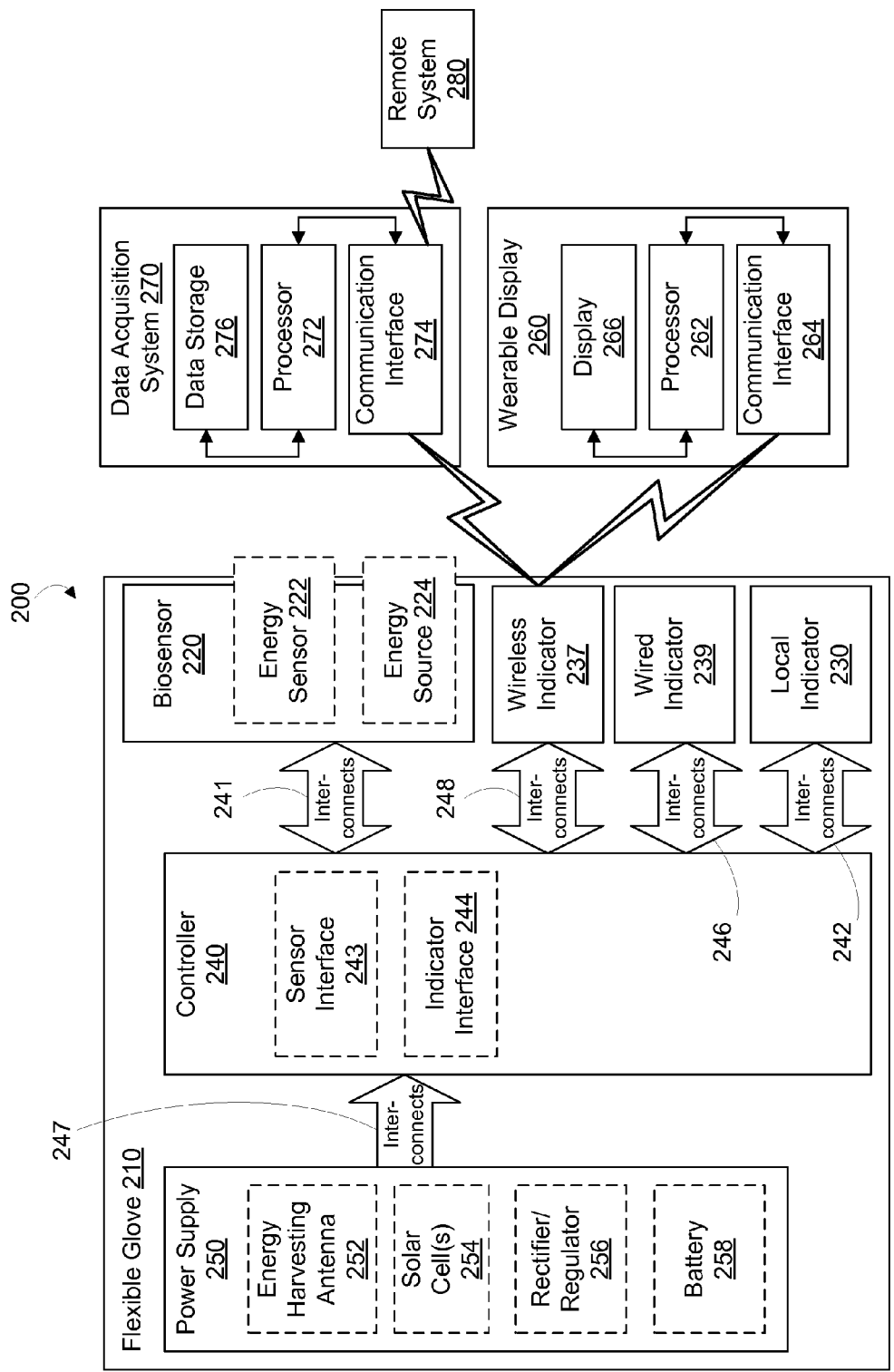

SMART SURGICAL GLOVE

BACKGROUND

Unless otherwise indicated herein, the materials described in this section are not prior art to the claims in this application and are not admitted to be prior art by inclusion in this section.

A number of scientific methods have been developed to detect and/or measure one or more properties of tissues of a person's body. The one or more properties could be any properties that could indicate or infer a medical condition or health state of the tissue and/or of the person. The one or more properties could be a temperature, electrical impedance or impedance spectrum, compliance, magnetic resonance properties (e.g., T1, T2 times), opacity to X-rays, degree of fluorescence and/or fluorescent spectrum, or some other property or properties. The one or more properties could be related to the presence, concentration, or other properties of an analyte. The analyte could be any substance that, when present in or absent from a person's body and/or tissues, or present at a particular concentration or range of concentrations, may be indicative of a medical condition or health state of the tissue and/or of the person. The one or more analytes could include enzymes, reagents, hormones, proteins, cells or other molecules. For example, the analytes could be cancer cells in a tissue of a human body and the detected properties could be related to the presence of cancer cells (e.g., a temperature of a cancer cell mass that is detectably different from a temperature of non-cancerous tissue, the presence of a fluorescent, X-ray, magnetic resonance, or other label that selectively interacts with cancer cells, an increased concentration of an angiogenesis-stimulating agent).

During a surgical intervention, a surgeon can rely on his/her senses (sight, touch, etc.) to detect one or more properties of tissue. The surgeon could rely on these senses to determine how to perform the surgical intervention, e.g., where to make an incision to access deeper tissues, or to excise diseased, necrotic, cancerous, or otherwise unhealthy tissue while leaving bordering healthy tissue intact. The surgeon can rely on imaging information generated by imaging modalities (e.g., X-ray, CT, MRI, ultrasound) to determine the location, extent, or other properties of target tissue based on relationships between the imaging information and anatomical information made available to the surgeon directly by the surgeon's senses. Additionally or alternatively, markers, fiducials, or other registration artifacts can be used to correlate imaging information with anatomical information directly available to the surgeon during the surgical intervention.

SUMMARY

Some embodiments of the present disclosure provide a device including: (i) a glove, wherein the glove comprises a flexible material, wherein the glove is configured to be worn on a hand, wherein the glove is configured to substantially prevent the passage of microorganisms from the inside of the glove to the outside of the glove through the flexible material; (ii) an energy sensor, wherein the energy sensor is disposed on the glove, wherein the energy sensor is configured to detect energy received from a target tissue proximate to the energy sensor; (iii) an energy source, wherein the energy source is disposed on the glove, wherein the energy source is configured to emit energy toward the target tissue proximate to the energy sensor; (iv) an indicator, wherein the indicator is disposed in the glove; and a controller, wherein the controller is disposed in the glove, wherein the controller is configured to: (a) operate the energy source to emit energy toward the target tissue proximate to the energy sensor, (b) operate the energy sensor to detect energy received from the target tissue proximate to the energy sensor in response to the energy source emitting energy, (c) determine one or more properties of the target tissue proximate to the energy sensor based on one or more properties of the energy received from the target tissue proximate to the energy sensor in response to the energy source emitting energy, and (d) operate the indicator to indicate the determined one or more properties of the target tissue proximate to the energy sensor.

Some embodiments of the present disclosure provide a device including: (i) a wireless receiver, wherein the wireless receiver is configured to receive a wireless signal from a wearable device that comprises: (a) a glove, wherein the glove comprises a flexible material, wherein the glove is configured to be worn on a hand, wherein the glove is configured to substantially prevent the passage of microorganisms from the inside of the glove to the outside of the glove through the flexible material; (b) an energy sensor, wherein the energy sensor is disposed on the glove, wherein the energy sensor is configured to detect energy received from a target tissue proximate to the energy sensor; (c) an energy source, wherein the energy source is disposed on the glove, wherein the energy source is configured to emit energy toward the target tissue proximate to the energy sensor; (d) a wireless transmitter, wherein the wireless transmitter is disposed in the glove, wherein the wireless transmitter is configured to transmit a wireless signal to the receiver; and (e) a controller, wherein the controller is disposed in the glove, wherein the controller is configured to: (1) operate the energy source to emit energy toward the target tissue proximate to the energy sensor, (2) operate the energy sensor to detect energy received from the target tissue proximate to the energy sensor in response to the energy source emitting energy, (3) determine one or more properties of the target tissue proximate to the energy sensor based on one or more properties of the energy received from the target tissue proximate to the energy sensor in response to the energy source emitting energy, and (4) operate the wireless transceiver to transmit the wireless signal to the receiver, wherein the wireless signal conveys information related to the determined one or more properties of the target tissue proximate to the energy sensor; and (ii) an indicator, wherein the indicator is configured to indicate the determined one or more properties of the target tissue proximate to the energy sensor based on the received wireless signal.

Some embodiments of the present disclosure provide a method including: (i) mounting a wearable device to a hand of a wearer, wherein the wearable device comprises: (a) a glove, wherein the glove comprises a flexible material and is configured to substantially prevent the passage of microorganisms from the inside of the glove to the outside of the glove through the flexible material; (b) an energy sensor, wherein the energy sensor is disposed on the glove, wherein the energy sensor is configured to detect energy received from a target tissue proximate to the energy sensor; (c) an energy source, wherein the energy source is disposed on the glove, wherein the energy source is configured to emit energy toward the target tissue proximate to the energy sensor; (d) an indicator, wherein the indicator is disposed in the glove; and (e) a controller, wherein the controller is disposed in the glove, wherein the controller is configured to operate the energy sensor, the energy source, and the indicator; and (ii) positioning the energy sensor proximate to a target tissue; (iii) operating the energy source to emit energy toward the target tissue; (iv) operating the energy sensor to detect energy received from the target tissue in response to the energy source emitting energy; (v) determining one or more properties of the target tissue based on one or more properties of the energy received from the target tissue in response to the energy source emitting energy; and (vi) operating the indicator to indicate the determined one or more properties of the target tissue.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2 is a functional block diagram of an example wearable system for measuring one or more properties of a biological tissue and indicating the measured one or more properties.

DETAILED DESCRIPTION

Figure 1A:
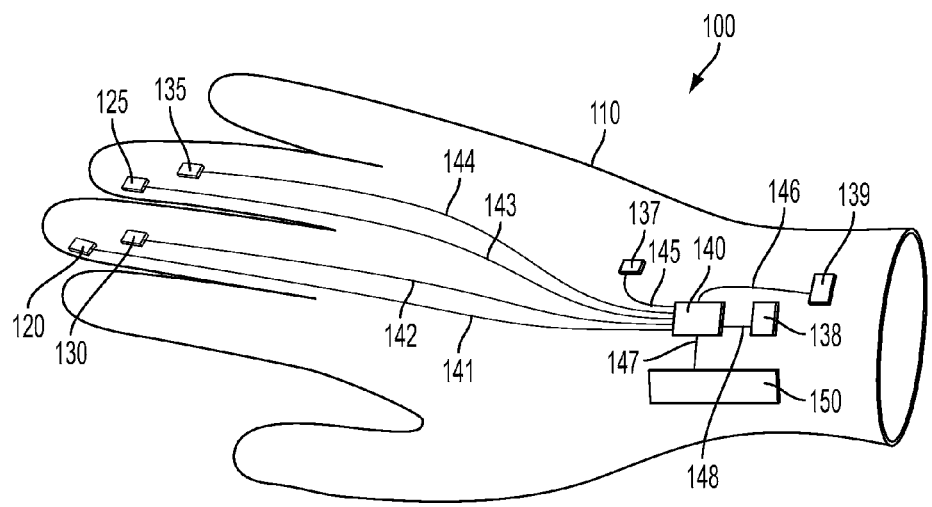
FIG. 1A illustrates an example wearable system that includes sensors, indicators, and a controller.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

While effecting a surgical intervention on a patient, a surgeon can wear flexible, sterile gloves on his/her hands to avoid introducing infectious microorganisms from the surgeon's hands to the patient. The gloves can be highly compliant or otherwise configured to allow the surgeon to use his/her hands to detect subtle differences in the compliance or other properties (e.g., texture, temperature, pulsing of blood due to perfusion) of tissues of the patient. These differences in tissue, in addition to differences in tissue detected visually, can guide the surgeon in performing the surgical intervention. The surgeon can also rely on information about the tissue generated by imaging modalities (e.g., X-ray, CT, MRI) do determine the location and other information about tissues of the patient.

However, these sources of information can be incomplete (e.g., low-resolution), obsolete (i.e., no longer representative of the tissues of the patient), difficult to correlate with the surgeon's experience of the tissues of the patient (e.g., landmarks in the imaging information may be difficult for the surgeon to correspond to features of the tissues observed by the surgeon), or otherwise insufficient to reliably guide the actions of the surgeon. Sensors and other systems could be added to the gloves worn by the surgeon and could be configured to augment the senses of the surgeon and/or provide additional information about the tissues of the patient, in real-time or in nearly real-time, to guide the actions of the surgeon.

Such gloves may be referred to herein as smart gloves. Smart gloves can include a sensor configured to detect some property or properties of tissues of a patient when those tissues are proximate to the sensor (e.g., when the wearer localizes the sensor proximate to the tissue). Smart gloves can additionally include an indicator configured to indicate the detected property or properties to the wearer directly (e.g., by causing the wearer to experience an informative sensation using means disposed in or on the smart glove) or indirectly (e.g., transmitting information about the detected property or properties to some other system configured to cause the wearer to experience an informative sensation and/or to a system configured to record, analyze, or perform some other operation related to the transmitted information). The smart glove could also include other elements, e.g., a controller to operate other elements of the smart glove, a battery to power elements of the smart glove, or other additional elements.

Elements of the smart glove could be disposed inside, outside, or wholly or partially embedded within the flexible material of the glove. The smart glove could include a connector, tether, or other means to connect the smart glove to other systems, e.g., a watch worn by the wearer and configured to power the smart glove, to indicate the detected property or properties, or to enable some other function.

The sensor could be configured in a variety of ways to detect a variety of properties of a tissue of a patient. The sensor could include light sensors, infrared sensors, ultraviolet sensors, cameras, optics, filters, temperature sensors, force sensors, strain sensors, electrodes and voltammeters, magnetic sensors, mass spectrometers, or other sensors, elements, and/or combinations of the above. Further, the glove could include active elements (e.g., light sources, electromagnetic field emitters, heating elements, driven radio frequency (RF) and/or microwave antennas, or other energy sources) that could be operated to enable the detection of one or more properties of the tissue of the patient. In some examples, a smart glove could include a light source configured to illuminate the tissue, and the illumination could cause elements of the tissue to reflect, refract, scatter, polarize, absorb and fluorescently re-emit, or otherwise interact with the illumination such that the sensor could detect one or more properties of the tissue. For example, the smart glove could include a light source and an electromagnetic field emitter, and the sensor could be a light sensor, and the sensor, light source, and electromagnetic field emitter could be operated to optically detect a magnetic resonance spectrum of elements of the tissue.

The smart glove could be configured to operate in combination with a contrast agent or other biological marker introduced into the body of a patient to enable the detection of one or more properties of a tissue of the patient. In some examples, the contrast agent could be configured to selectively bind to an analyte of interest (e.g., cancer cell) and elements of the smart glove could be configured to detect the presence of the contrast agent. For example, the contrast agent could include a fluorophore, and the smart glove could include a light source configured to emit illumination into the tissue such that the fluorophore in the tissue emitted light in response to the illumination. The sensor could be a light sensor configured to detect the light emitted by the fluorophore in response to the illumination. The contrast agent could include fluorophores, color centers, pigments, chromophores, magnetic moieties, radioisotopes, or other elements to enable detection of the presence or some other property or properties of the contrast agent by the smart glove.

The smart glove could include a variety of different indicators configured to indicate one or more properties of a tissue of a patient detected by the sensor to the wearer of the smart glove. In some examples, the smart glove could include an indicator configured to induce a sensation in the hand of the wearer. For example, the indicator could include a haptic element (e.g., a vibrator, electrodes, a modulated-compliance element) or a heat-emitting element configured to deliver a haptic sensation or heat sensation, respectively, to the hand of the wearer. In another example, light emitters disposed in the smart glove and configured to deliver a visual sensation to the wearer when the wearer is looking at the smart glove. Additionally or alternatively, the indicator could be configured to indicate the detected one or more properties of the tissue (e.g., by transmitting a wireless signal) to another system that is configured to induce a sensation in the wearer of the smart glove (e.g., a wearable display unit configured to receive the wireless signal and to generate a display that is viewable by the wearer and that is related to the detected one or more properties of the tissue).

The smart glove could include additional elements. For example, the smart glove could include elements configured to deliver a medical treatment to tissues of the patient. In one example, the smart glove could include an RF emitter or laser configured to ablate or otherwise damage tissue. The RF emitter or laser could be operated by the wearer of the smart glove to destroy cancerous or otherwise unhealthy tissue of the patient. This operation could be related to information about the tissue detected by the sensor and indicated to the wearer by the smart glove.

II. Example Smart Surgical Gloves

FIG. 1A is an illustration of an example smart surgical glove 100. The smart surgical glove 100 includes a flexible substrate 110 shaped to be worn on a hand of a wearer. Disposed on or within the flexible substrate 110 are biosensors 120, 125, local indicators 130, 135, 137, a wireless indicator 138, a wired indicator 139, a power supply 150, and a controller 140. Electronic components are electrically connected by interconnects 141, 142, 143, 144, 145, 146, 147, 148.

The controller 140 is configured to operate the various biosensors 120, 125 and to operate the various indicators 130, 135, 137, 138, 139 to indicate information about a tissue or other environment proximate to the biosensors 120, 125. In some examples, the biosensors 120, 125 could detect one or more properties of the tissue or other environment (e.g., a thermal and/or electrical conductivity, the presence of cancer cells, pH, vascularity, the presence of a marker chemical) that cannot be directly sensed by the natural senses of a human, and the controller could operate one or more of the indicators 130, 135, 137, 138, 139 to cause a sensation in a human (e.g., a temperature sensation, a visual stimulus, a vibration or other haptic stimulus) related to the detected one or more properties such that the smart surgical glove 100 allows the human to indirectly sense the detected one or more properties of the tissue or other environment.

Additionally or alternatively, the controller 140 could operate the biosensors 120, 125 and indicators 130, 135, 137, 138, 139 to amplify or otherwise enhance a sense of a human. For example, a biosensor could detect a temperature, and an indicator could generate a heat such that a difference in temperature sensed by the biosensor caused a greater difference in temperature to be sensed by skin of a human proximate to the indicator. Thus, the smart surgical glove 100 could be operated to allow a wearer to detect smaller differences in properties of biological tissues or other environments (e.g., compliance, temperature, surface smoothness or other textural properties) than the wearer could sense using their natural senses.

The controller 140 is generally configured to operate the biosensors 120, 125 to detect one or more properties of a tissue or other environment proximate to the biosensors 120, 125. This can include detecting a voltage, a current, a resistance, or some other electrical output of the biosensors 120, 125. This could also include setting one or more parameters of the biosensors 120, 125, for example, an amplification factor, a bandwidth, an offset, an operating frequency, an electrode potential difference, a bias current, a sensitivity, a resolution, or some other property of the biosensors 120, 125 according to an application. For example, the controller 140 could operate a light sensor of the biosensors 120, 125 to remove an offset from an output of the light sensor that is related to an ambient level of light in the environment proximate to the light sensor, a temperature-dependent voltage offset of the light sensor, or some other property of the light sensor and/or environment proximate to the light sensors.

The controller 140 operating the biosensors 120, 125 to detect one or more properties of a tissue or other environment can also include operating energy emitters (e.g., light emitters, infrared emitters, ultraviolet emitters, RF emitters, heat sources) of the biosensors 120, 125 to enable active sensing of one or more properties of an environment proximate to the biosensors 120, 125. In some examples, the biosensors 120, 125 could include a light source that is configured to illuminate a fluorophore, chromophore, or other element of interest in a tissue, and a light sensor of the biosensors 120, 125 could be configured to detect a light that is received from the tissue and that has one or more properties related to the fluorophore, chromophore, or other element of interest. The fluorophore, chromophore, or other element of interest could be introduced into the tissue (or into another environment of interest) to enable sensing of one or more properties of interest of the tissue. For example, a fluorophore configured to selectively interact with cancer cells could be introduced into a tissue, and detection of the presence of the fluorophore could be performed to enable to determination that cancer cells are present in the tissue. Other configurations and operations of biosensors are anticipated.

The smart surgical glove 100 could be configured to enable other applications. Information from the biosensors 120, 125 could be indicated to other systems (e.g., a computer, a server, a surgical robot, a head mounted display (HMD), a wearable device) using the wireless indicator 138 and/or the wired indicator 139. The local indicators 130, 135, 137 could be operated to indicate information received through the wireless indicator 138, wired indicator 139, or some other communications element of the smart surgical glove 100. For example, information from an imaging system (e.g., an MRI device) about a tissue could be indicated to a wearer using the local indicators 130, 135, 137 when the smart surgical glove 100 or elements thereof (e.g., a fingertip) are proximate to the tissue (e.g., when the fingertip is proximate to a tumor mass detected by the MRI device, an indicator in the fingertip could be activated to induce a sensation in the corresponding finger of a wearer, informing the wearer that the fingertip is proximate to the detected tumor mass). In some examples, biosensors 120, 125 or other elements (e.g., hand joint flex sensors embedded in the flexible material 110) of a smart surgical glove 100 could be operated to provide the wearer with control of functions of the smart surgical glove 100 and/or other systems in communication with the smart surgical glove 100. For example, the wearer bending a particular joint, forming a specified pose with their hand, or performing some other task that is detectable by the smart surgical glove 100 could be detected, and that detection could cause operating mode or function of the smart surgical glove 100 and/or other systems to be executed. In some examples, properties of the tissue or other environment proximate to the biosensors 120, 125 could be recorded for later use or for analysis during a surgical intervention or other activity in order to inform the performance of the surgical intervention or other activity.

To facilitate being worn on a hand, the flexible material 110 can have a shape similar the outer surface of a human hand. The flexible material 110 could have a size equal to one of a set of standardized glove sizes, or could be custom-made to fit an individual hand. The flexible material 110 could be injection-molded, formed by dipping a hand-shaped mold into a bath of liquid and cured into a flexible material, or formed by some other method. Other elements of the smart surgical glove 100 could be disposed on/in/within the flexible material 110 when the flexible material 110 is formed, or at a later time. The flexible material 110 includes one or more surfaces suitable for mounting, embedding and/or disposing power supply 150, controller 140, biosensors 120, 125, indicators 130, 135, 137, 138, 139, and interconnects 141, 142, 143, 144, 145, 146, 147, 148.

Components of the smart surgical glove 100 could be adhered to an outside or inside surface of the flexible material 110 using an adhesive, clips, or by some other method. Interconnects 141, 142, 143, 144, 145, 146, 147, 148 or other electrical components could be patterned on an inside or outside surface of the flexible material 110 by photoresists, masks, deposition techniques, sputtering, plating techniques, and/or some other process whereby conductive materials (e.g., gold, platinum, palladium, titanium, copper, aluminum, silver, metals, other conductive materials, combinations of these, etc.) are selectively deposited on the flexible material 110 of the smart surgical glove 100. Other components (e.g., 150, 140, 120, 125, 130, 135, 137, 138, 139) could then be disposed on the flexible material 110 in electrical contact with the deposited conductive materials (e.g., by flip-chip mounting). Additionally or alternatively, the interconnects 141, 142, 143, 144, 145, 146, 147, 148 could be discrete wires disposed in, on, or within the flexible material 110. The interconnects could include strain reliefs in the form of loops, serpentine patterns, or other geometries of wires and/or patterned conductor traces such that the interconnects 141, 142, 143, 144, 145, 146, 147, 148 can withstand flexing of the flexible material 110.

Interconnects and/or components deposited on the flexible material 110 could be covered in a protective layer. The protective layer could be a conformal coating that is sprayed or otherwise applied to the flexible material 110. The protective layer could be adhered to the flexible material 110 using an adhesive. The interconnects and components could be disposed on a first formed layer of the flexible material 110, and a second layer could be formed onto the first formed layer, protecting the interconnects and other components.

The flexible material 110 could be composed of a variety of flexible, substantially microbe-impermeable materials, including but not limited to latex, vinyl, isoprene, nitrile rubber, neoprene, or other synthetic or natural rubbers or other polymers or combinations thereof. The flexible material could include a variety of hypoallergenic or otherwise biocompatible materials and/or coatings. The flexible material 110 could include a powder or other coating or treatment to facilitate mounting the smart surgical glove 100 on a hand of a wearer. The material(s) composing the flexible material 110 could be resilient against chemical, radiation, heat, or other methods of sterilization.

The smart surgical glove 100 could be configured for single-use or for multiple re-use. In examples where the smart surgical glove 100 is configured for re-use, elements of the smart surgical glove 100 (e.g., the flexible material 110) could be composed of materials that could be re-sterilized by a variety of methods, including but not limited to high-pressure steam sterilization, ethylene oxide sterilization, ozone sterilization, hot bead sterilization, gamma irradiation, ultraviolet irradiation, or other forms of chemical or physical sterilization.

In some examples, some of the illustrated components of the smart surgical glove 100 could be disposed on/within the flexible material 110 while other components are located elsewhere or are otherwise removably attached to the components on/within the flexible material 110. In some examples, biosensor(s), local indicator(s), a connector, and interconnects between the connector and the biosensor(s) and local indicator(s) could be disposed on a flexible material formed in the shape of a glove. An electronics module that includes a controller, a power source, and other components (e.g., a wireless indicator, a wired indicator) could be configured to be removably connected to the connector such that the controller can operate the biosensor(s) and indicator(s) to provide the functions and enable the applications described herein. In some examples, the electronics module is included in a watch or other wearable device and connected to the connector via a tether, a cable, or some other flexible or rigid interconnection. In some examples, the flexible material formed in the shape of a glove and components disposed thereon are configured for a single use and the electronics module is configured to be re-used (e.g., to be re-sterilized through one or more sterilization processes). Other partitionings and configurations of components of a smart surgical glove are anticipated.

The biosensors 120, 125 could include any sensors configured to detect one or more properties of a tissue or other environment. The biosensors 120, 125 could include light sensors, infrared sensors, color sensors, ultraviolet sensors, light filters, polarizing filters, cameras, interferometers, or other optical detectors or components related to optical detection. The biosensors 120, 125 could include electrodes, reference electrodes, working electrodes, pH-sensitive electrodes, layers of chemically-selective reagents, layers of chemically-selective ionophores, chemically-selective metal oxide layers, current sources, voltage sources, or other components related to detecting chemicals in and/or electrophysiological properties of (e.g., conductivity, impedance spectrum) the tissue or other environment. The biosensors 120, 125 could include strain gauges, piezo elements, electroactive polymers, or other components related to determining a compliance, a force, a vibration, or some other mechanical property or properties of the tissue or other environment. The biosensors 120, 125 could include Geiger tubes, magnetic field sensors, electric field sensors, thermometers, mass spectrometers, magnetic resonance sensors, energy sensors, or any kind of sensor configured to detect one or more properties of the tissue or other environment.

The biosensors 120, 125 could additionally include components configured to emit and/or inject energy toward/into a tissue or other environment to enable active sensing of one or more properties of the tissue or other environment. That is, the biosensors 120, 125 could emit and/or inject energy toward/into the tissue or other environment and could measure one or more properties of the tissue or other environment by detecting a change in the tissue or other environment produced by the emitted and/or injected energy. In some embodiments, this could include injecting a current into the environment using a first electrode and sinking the current out of the environment using a second electrode. A voltage between the first and second electrodes could be measured to determine an impedance or some other property of the environment. In some embodiments, a light having a specified wavelength could be emitted to illuminate the environment, and a light sensor could be used to detect one or more properties of light emitted by fluorophores of the environment in response to the illumination. Other types of emitted and/or injected energy and corresponding detected properties are anticipated.

In some examples, a biosensor could include a light source to emit light having a specified wavelength such that fluorophores or other optically active elements of the tissue or other environment proximate to the light source interacted with the emitted light and caused a light sensor of the biosensor to receive light from the fluorophores or other optically active elements. For example, the tissue or other environment could include a fluorescent marker, and the light source could be configured to emit light having a specified wavelength to excite the fluorescent marker. The light sensor could be configured to detect light emitted by the fluorescent marker in response to being excited by light from the light source. The fluorescent marker could be configured to bind to an analyte of interest (e.g., a cancer cell) and detection of the fluorescent marker could be used to determine the presence and/or concentration of the analyte of interest. In some examples, the light source could be configured to emit light having one or more specified wavelengths that could be scattered by elements of the tissue or other environment, and the light sensor could detect one or more properties of the scattered light related to one or more properties of the tissue or other environment. For example, the light source could emit light having two specified wavelengths (e.g., a red wavelength (e.g., 660 nanometers) and a near-infrared wavelength (e.g., 910 nanometers)) related to differences in the absorption spectra of oxygenated and deoxygenated hemoglobin, and the light sensor could detect a difference in absorption of the two specified wavelengths sufficient to determine a level of oxygenation of blood in the tissue or other environment.

In some embodiments, the biosensors 120, 125 can be positioned near fingertips of the smart surgical glove 100 (e.g., the tips of the middle and ring fingers, respectively, in the example illustrated in FIG. 1A) such that a wearer of the smart surgical glove 100 could direct their fingertip toward a tissue or other environment of interest such that a corresponding biosensor 120, 125 on the fingertip could detect one or more properties of the tissue or other environment of interest. For example, biosensor 120 is disposed on or within the tip of a middle finger of the flexible material 110. In some embodiments, biosensors could be disposed on other finger tips (e.g., biosensor 125 on the tip of the ring finger of the flexible material 110), or on other regions of the fingers and/or hand of the smart surgical glove 100 according to an application.

Biosensors of a smart surgical glove 100 could be configured to be small, to have a compliance similar to the compliance of the flexible material 110, or to be otherwise configured to minimally impact the tactile senses of a wearer of the smart surgical glove 100. For example, one or more of the biosensors could have a size less than 100 micrometers. In some examples, one or more components of a biosensor could be adhered or otherwise disposed on an outside surface of the flexible material 110. In some examples, one or more components of a biosensor could be wholly or partially embedded in the flexible material 110.

In some embodiments, the biosensors 120, 125 can include multiple components disposed at multiple locations on or near the smart surgical glove 100 and/or disposed elsewhere. The biosensors 120, 125 could include light pipes, waveguides, tubes, pipes, microfluidic components, vacuum lines, or other components to enable elements of an individual biosensor to be located at different locations. In some embodiments, one or more components of a biosensor could be bulky or otherwise unsuited to being disposed at a specified location on the smart surgical glove 100 (e.g., on a fingertip). In those embodiments, one or more bulky elements could be disposed at a location other than the specified location and the biosensor could include components to enable the biosensors to detect one or more properties of a tissue or other environment proximate to the specified location on the smart surgical glove 100. For example, a light emitter could be disposed near a cuff of the smart surgical glove 100 and a light pipe could be configured to conduct light from the light emitter to a fingertip of the smart surgical glove 100; conversely, a light pipe could conduct light received from a tissue or other environment proximate to a fingertip of the smart surgical glove 100 to a light sensor located elsewhere on the smart surgical glove 100 or located on some other device connected to the smart surgical glove 100. In another example, a vacuum or other fluid-transporting line, pipe, or tube could be used to transport energy and/or matter (e.g., a fluid sample) from a location on the smart surgical glove 100 (e.g., a fingertip) to another location (e.g., a mass-spectrometer or other sample-analysis component disposed on the smart surgical glove 100 or disposed in some other location and connected to the smart surgical glove 100). Other embodiments are anticipated.

Figure 1B:
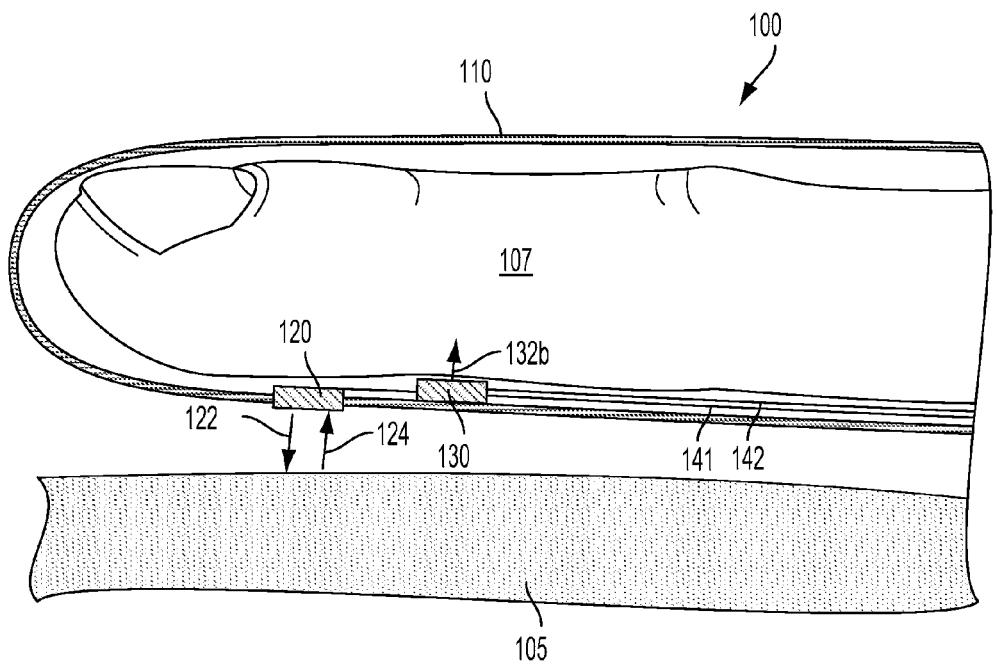
FIG. 1B is a cross-section view through a finger of the example wearable system of FIG. 1A.

FIG. 1B illustrates an example cross-section view of a finger of the wearer 107 inside a fingertip of the flexible material 110 of the smart surgical glove 100. A biosensor 120 is partially embedded in the flexible material 110 at the fingertip of the smart surgical glove 100 and is being operated to emit energy 122 into a target tissue 105 located proximate to the biosensor 120. The biosensor 120 detects one or more properties of received energy 124 from the target tissue 105 that is emitted, reflected, scattered, or otherwise emanating from the target tissue 105 in response to the emitted energy 122. The emitted energy 122 could be visible light, ultraviolet light, infrared light, microwaves, oscillating electromagnetic fields, energetic particles (e.g., alpha particles, beta particles, ions), or any other kind of energy emitted and/or injected into the target tissue 105, and the received energy 124 could be any detectable energy or property of the tissue 105. Alternatively, the biosensor 120 could be a passive sensor that detects energy from tissue 105 without emitting or injecting energy into tissue 105.

Indicators of the smart surgical glove 100 (not including any wireless (e.g., 138) and/or wired (e.g., 139) indicators) could include any transducers or other electronic or mechatronic elements configured to cause a wearer of the smart surgical glove to experience a sensation.

The indicators could be configured to cause a haptic, a tactile, a temperature, or some other sensation in skin of the wearer that is proximate to the indicator. The indicators could include piezo elements, electroactive polymers, vibrators, resistive heating elements, electrodes configured to inject a current and/or apply a voltage to skin, or other elements. FIG. 1B illustrates an example indicator 130 configured to apply an oscillating mechanical force 132b to skin of the finger of the wearer 107 sufficient to induce a sensation in the skin of the wearer 107. In other embodiments, the oscillating mechanical force 132b could be a vibration, an electrical current, a heat flux, an electrical voltage, or some other electrical, chemical, optical, and/or mechanical energy or force sufficient to induce a sensation in the skin of the wearer 107.

In some embodiments, an indicator (e.g., 130) is operated to indicate information detected using a single proximate biosensor (e.g., 120). In some embodiments, one or more indicators are operated to indicate information from one or more biosensors. In some examples, a set of biosensors could be configured to determine the compliance of tissue proximate to the set of biosensors, and a single indicator could be operated to indicate the determined compliance. In some examples, a biosensor could be configured to determine an orientation of collagen in tissue proximate to the biosensor, and a set of indicators could be operated to indicate the determined orientation (e.g., by stimulating a line of skin parallel to the determined orientation). In some examples, other information could be indicated to the wearer 107 using indicators disposed in the smart surgical glove 100. For example, information from some other imaging system (e.g., a CT scanner, an MRI system) could be transmitted to the smart surgical glove 100 and the indicators (e.g., 130) of the smart surgical glove 100 could be operated based on the received information. For example, the indicator could be operated to indicate to the wearer 107 when the wearer's 107 fingertip is proximate to the location of a tumor mass detected using the other imaging system. Other configurations and operations of biosensors and indicators of a smart surgical glove 100 are anticipated.

Figure 1C:
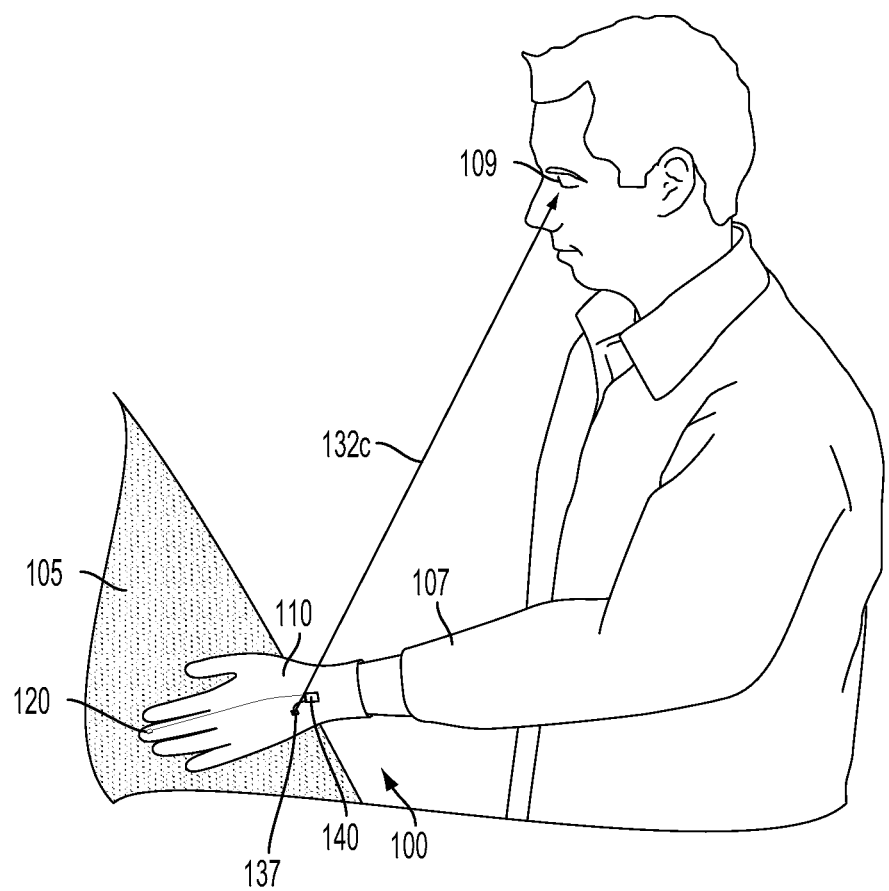
FIG. 1C illustrates the example wearable system of FIG. 1A indicating information visually to a wearer.

The indicators could induce a visual stimulus by emitting a light, changing a reflectivity, changing a color, or changing some other optical property. Such indicators could include light emitting diodes (LEDs), liquid crystals, polarizers, reflectors, lenses, displays, e-Ink, e-Paper, or other elements having optical properties that can be controlled. For example, indicator 137 includes an LED configured to emit a visible light. This is illustrated in FIG. 1C, which illustrates the smart surgical glove 100 being worn by a wearer 107. The wearer has positioned his hand such that a biosensor 120 is positioned proximate to a tissue 105 under study. The controller 140 is operating the biosensor 120 to detect one or more properties of the tissue 105 and operating the indicator 137 to emit a light 132c that can be sensed by the eye 109 of the wearer when the wearer's gaze is directed toward the smart surgical glove 100.

In some embodiments, the smart surgical glove 100 could include a plurality of indicators and/or biosensors, respectively. For example, the smart surgical glove 100 could include a plurality of force sensors disposed on a fingertip of the flexible material 110 and the controller 140 could determine a property of tissue in contact with the fingertip (e.g., a compliance of the tissue) and could operate an indicator disposed in the fingertip to indicate the determined property. In another example, the smart surgical glove 100 could include a plurality of fluorophore detectors (i.e., a plurality of light sources and corresponding light sensors configured to illuminate and to receive light emitted from fluorophores in tissue proximate to the light sources and light sensors, respectively) disposed across a fingertip. The smart surgical glove 100 could include a plurality of haptic indicators (i.e., indicators configured to apply a force, vibration, electrical stimulus, or other stimulus to skin of a wearer to induce a haptic sensation) disposed across the fingertip at locations corresponding to the locations of the fluorophore detectors, and the controller 140 could operate an individual haptic indicator to indicate a property of tissue detected by a corresponding fluorophore detector. Other arrangements and methods of operation of one or more indicators and one or more biosensors are anticipated.

The wireless indicator 138 and wired indicator 139 enable the smart surgical glove 100 to indicate determined properties of tissues or other environments proximate to biosensors of the smart surgical glove 100 to a variety of remote systems. In some embodiments, the wireless indicator 138 could transmit radio, microwave, or other electromagnetic signals to remote systems indicating the determined information. In some embodiments, the wired indicator 139 could transmit electrical and/or optical signals over a cable, tether, fiber, or other physical interconnection to indicate the determined information. Remote systems could include computers, smart phones, wearable devices, displays, data loggers, medical imaging devices, medical and/or surgical devices (e.g., RF ablation probes, surgical robots), or other systems. Remote systems could include any device that includes a wireless receiver configured to receive wireless signals from the wireless indicator 138 and an indicator (e.g., a display) configured to indicate determined properties of tissues or other environments that are included in the received wireless signals.

Figure 1E:
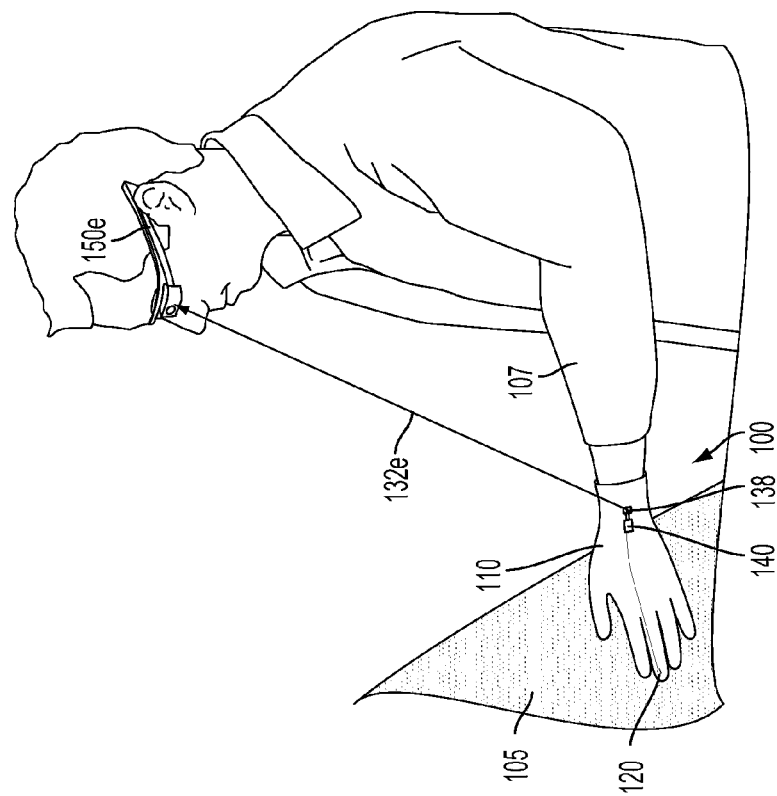
FIG. 1E illustrates the example wearable system of FIG. 1A indicating information to a head-mounted display.
Figure 1D:
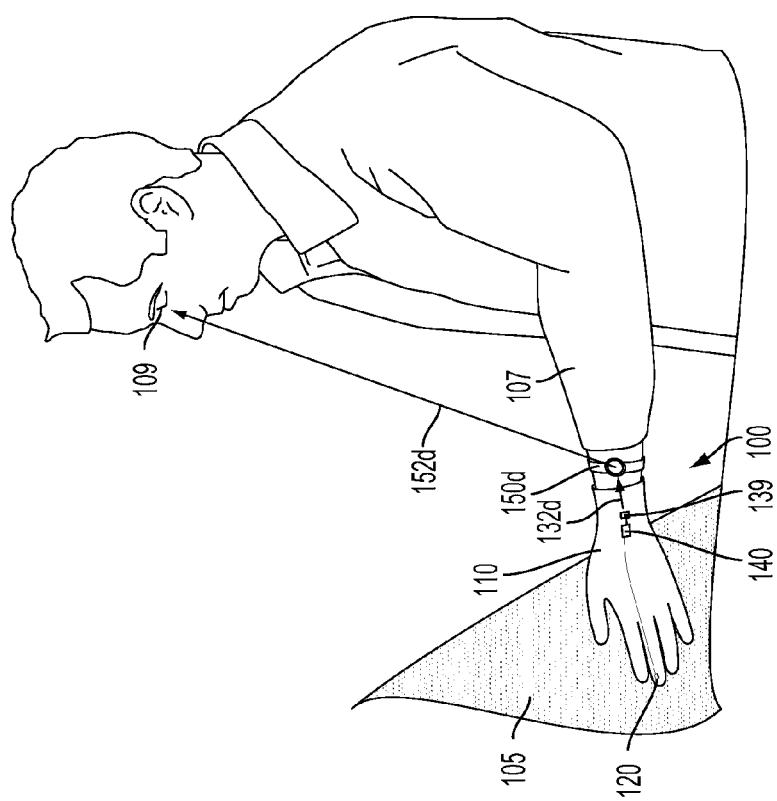
FIG. 1D illustrates the example wearable system of FIG. 1A indicating information to another wearable system.

FIG. 1D illustrates the smart surgical glove 100 being worn by a wearer 107. The wearer has positioned his hand such that a biosensor 120 is positioned proximate to a tissue 105 under study. The controller 140 is operating the biosensor 120 to detect one or more properties of the tissue 105 and operating the wired indicator 139 to send an electrical signal over a tether 132d to a wearable device 150d. The wearable device 150d includes an indicator configured to emit a light 152d that has one or more properties related to the detected one or more properties of the tissue 105 and that can be sensed by the eye 109 of the wearer when the wearer's gaze is directed toward the wearable device 150d. The smart surgical glove 100 could additionally or alternatively indicate information to the wearable device 150d using the wireless indicator 138 in embodiments wherein the wearable device 150d include a corresponding wireless receiver.

FIG. 1E illustrates the smart surgical glove 100 being worn by a wearer 107. The wearer has positioned his hand such that a biosensor 120 is positioned proximate to a tissue 105 under study. The controller 140 is operating the biosensor 120 to detect one or more properties of the tissue 105 and operating the wireless indicator 138 to send an electromagnetic signal 132e to a head-mounted display 150e. The head-mounted display 150e includes a display that can display to the wearer information related to the detected one or more properties of the tissue 105. In some embodiments, the biosensor 120 could include a camera, and the display of the head-mounted display 150e could be operated to display an image corresponding to an image detected by the camera of the biosensor 120.

Note that the smart surgical glove 100 could indicate information to wearable or other remote devices (e.g., 150d, 150e) indirectly. For example, the smart surgical glove 100 could indicate information to a central server or other communication-enabled device, and the server or other communication-enabled device could transmit the indicated information to other devices or systems (e.g., 150d, 150e). The central server or other communication-enabled device could additionally perform some computation and/or filtering on the indicated information and/or add information from other sources (e.g., imaging data from CT scans or MRI scans) before transmission to other devices or systems (e.g., 150*d*, 150*e*).

Other configurations and applications of a smart surgical glove or other instrumented glove that includes sensors and indicators are also anticipated. Embodiments described herein could additionally or alternatively be applied to detect one or more properties of materials and/or tissues in a variety of environments. The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, or some other environment. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., a fluorescent agent configured to selectively interact with an analyte of interest) to the environment.

III. Example Electronics Platform for a Smart Surgical Glove

FIG. 2 is a block diagram of a system 200 that includes a flexible glove 210 and a variety of components disposed in, on, or within the flexible glove 210. The flexible glove 210 is made of a flexible material formed to be worn on a human hand and to substantially prevent the passage of microorganisms from the inside of the glove (e.g., microorganisms present on a hand of a wearer). The system 200 additionally includes a power supply 250, a controller 240, a biosensor 220, a wireless indicator 237, a wired indicator 239, a local indicator 230, and interconnects 241, 242, 246, 247, and 248. The biosensor 220 and indicators 230, 237, 239 are operated by the controller 240. The power supply 250 supplies operating voltages to the controller 240, indicators 230, 237, 239, and/or the biosensor 220. The indicators 230, 237, 239 are operated by the controller 240 to communicate information to and/or from the system 200. The power supply 250, controller 240, biosensor 220, indicators 230, 237, 239, and interconnects 241, 242, 246, 247, 248 can all be situated on an inside surface of, on an outside surface of, and/or within the flexible material of the flexible glove 210. Because the system 200 includes electronics and takes the form of a glove configured to be worn on a hand of a wearer while the wearer performs a surgical intervention, it is also referred to herein as a smart surgical glove.

To facilitate being worn on a hand, the flexible glove 210 can have a shape similar to the outer surface of a human hand. The flexible glove 210 could have a size equal to one of a set of standardized glove sizes, or could be custom-made to fit an individual hand. The flexible glove 210 could be injection-molded, formed by dipping a hand-shaped mold into a bath of liquid and cured into a flexible material, or formed by some other method. Other elements of the system 200 could be disposed on/in/within the flexible glove 210 when the flexible glove 210 is formed, or at a later time. The flexible glove 210 could be composed of a variety of flexible, substantially microbe-impermeable materials, including but not limited to latex, vinyl, isoprene, nitrile rubber, neoprene, or other synthetic or natural rubbers or other polymers or combinations thereof. The flexible material could include a variety of hypoallergenic or otherwise biocompatible materials and/or coatings. The flexible glove 210 could include a powder or other coating or treatment to facilitate mounting the flexible glove 210 on a hand of a wearer. The material(s) composing the flexible glove 210 could be resilient against chemical, radiation, heat, or other methods of sterilization.

The flexible glove 210 includes one or more surfaces suitable for mounting, embedding and/or disposing power supply 250, controller 240, biosensor 220, indicators 230, 237, 239, and interconnects 241, 242, 246, 247, 248. Components of the system 200 could be adhered to an outside or inside surface of the flexible glove 210 using an adhesive, clips, or by some other method. Interconnects 241, 242, 246, 247, 248 or other electrical components could be patterned on an inside or outside surface of the flexible glove 210 by photoresists, masks, deposition techniques, sputtering, plating techniques, and/or some other process whereby conductive materials (e.g., gold, platinum, palladium, titanium, copper, aluminum, silver, metals, other conductive materials, combinations of these, etc.) are selectively deposited on the material of the flexible glove 210. Other components (e.g., 250, 240, 220, 230, 237, 239) could then be disposed on the flexible glove 210 in electrical contact with the deposited conductive materials (e.g., by flip-chip mounting). Additionally or alternatively, the interconnects 241, 242, 246, 247, 248 could be discrete wires disposed in, on, or within the flexible glove 210.

In some embodiments, the biosensor 220 can be positioned near a fingertip of the flexible glove 210 such that a wearer of the system 200 could direct their fingertip toward a tissue or other environment of interest such that the biosensor 220 could detect one or more properties of the tissue or other environment of interest. For example, the biosensor 220 could be disposed on or within the tip of an index finger of the flexible glove 210. In some embodiments, the biosensor 220 could be disposed on other finger tips, or on other regions of the fingers and/or hand of the flexible glove 220. In some embodiments, the biosensor 220 could include multiple components connected together (e.g., by a light pipe, conductors, tubes, pipes, or other components) such that the biosensor 220 can detect one or more properties of a tissue or other environment proximate to a first location while including one or more components disposed at a second location. The biosensor 220 could be configured to be small, have a compliance similar to the compliance of the flexible glove 210, or be otherwise configured to minimally impact the tactile senses of a wearer of the system 200. For example, the biosensor 220 could have a size less than 100 micrometers. In some embodiments, the biosensor 220 can include additional or alternate components. For example, the biosensor 220 could include a thermocouple, a galvanic sensor, a chemical sensor, or some other component(s) configured to detect one or more properties of a tissue or environment proximate to the biosensor 220.

The power supply 250 is configured to provide energy to power the controller 240, biosensor 220, and indicators 230, 237, 239. For example, a radio-frequency energy-harvesting antenna 252 can capture energy from incident radio radiation. Additionally or alternatively, solar cell(s) 254 ("photovoltaic cells") can capture energy from incoming ultraviolet, visible, and/or infrared radiation. Furthermore, an inertial power scavenging system can be included to capture energy from ambient vibrations. The energy harvesting antenna 252 can optionally be a dual-purpose antenna that is also used to communicate information to some external system (e.g., a data acquisition system 270 or wearable display 260). That is, the functions of the wireless indicator 237 and the energy harvesting antenna 252 can be accomplished with some of the same physical elements. The power supply 250 can additionally or alternatively include a battery 258. The battery 258 could be a single-use battery or could be rechargeable (e.g., by using energy harvested using the energy harvesting antenna 252, solar cells 254, or accessed through some other method, including but not limited to a wired tether between the system 200 and some external energy source).

A rectifier/regulator 256 can be used to condition the captured energy to a stable DC supply voltage on the interconnects 247 that is supplied to the controller 240. For example, the energy harvesting antenna 252 can receive incident radio frequency radiation. Varying electrical signals on the leads of the antenna 252 are output to the rectifier/regulator 256. The rectifier/regulator 256 rectifies the varying electrical signals to a DC voltage and regulates the rectified DC voltage to a level suitable for operating the controller 240. Additionally or alternatively, output voltage from the solar cell(s) 254 can be regulated to a level suitable for operating the controller 240. The rectifier/regulator 256 can include one or more energy storage devices to mitigate high frequency variations in the ambient energy gathering antenna 252 and/or solar cell(s) 254. For example, one or more energy storage devices (e.g., a capacitor, an inductor, etc.) can be connected in parallel across the outputs of the rectifier 256 to regulate the DC supply voltage on the interconnects 247 and configured to function as a low-pass filter. In embodiments including a rechargeable battery 258, the rectifier/regulator 256 can include circuitry for charging the battery 258.

The controller 240 is turned on when the DC supply voltage on the interconnects 247 is provided to the controller 240, and the logic in the controller 240 operates the biosensor 220 and indicators 230, 237, 239. The controller 240 can include logic circuitry configured to operate the biosensor 220 so as to interact with a tissue or other environment proximate to the biosensor 220. The interaction could involve the use of one or more components, such as an energy sensor 222 and an energy source 224, in the biosensor 220 to obtain input from and/or detect one or more properties of the tissue or other environment. Additionally or alternatively, the interaction could involve the use of one or more components, such as an RF ablation probe, to provide an output to the tissue or other environment.

In one example, the controller 240 includes a sensor interface module 243 that is configured to operate the biosensor 220. The biosensor 220 can be, for example, an active sensor that includes an energy source 224 and an energy sensor 222. Energy can be received by the energy sensor 222 from the tissue or other environment in response to emission of energy toward the tissue or other environment by the energy source 224. One or more properties of the received energy could be related to one or more properties of the tissue or other environment and could be detected by the energy sensor 222. In some embodiments, the sensor interface module 243 can include controllable current sources, controllable voltage sources, timers, feedback controllers, or other elements to control one or more properties of light emitted by the light source 224. In some embodiments, the sensor interface module 243 can include comparators, ADCs, feedback amplifiers, transimpedance amplifiers, or other elements to detect one or more properties of energy received by the energy sensor 222. In some embodiments, the sensor interface module 243 can include other electronic and/or mechatronic elements to enable to use of other components of the biosensor (e.g., radiation detectors, Geiger tubes, electrodes, chemical sensors, pH sensors, force sensors, conductivity sensors, temperature sensors).

Components of the biosensor 220 could be configured to interact with one or more chemicals, markers, cells, or other elements of the tissue or other target tissue. In some embodiments, the energy source 224 could be configured to emit light having a specified wavelength such that fluorophores or other optically active elements of the tissue or other environment proximate to the energy source 224 interacted with the emitted light and caused the energy sensor 222 to receive light from the fluorophores or other optically active elements. For example, the tissue or other environment could include a fluorescent marker, and the energy source 224 could be configured to emit light having a specified wavelength to excite the fluorescent marker. The energy sensor 222 could be configured to detect light emitted by the fluorescent marker in response to being excited by light from the energy source 224. The fluorescent marker could be configured to bind to an analyte of interest (e.g., a cancer cell) and detection of the fluorescent marker could be used to determine the presence and/or concentration of the analyte of interest. In another example, the energy source 224 could be configured to emit light having one or more specified wavelengths that could be scattered by elements of the tissue or other environment, and the energy sensor 222 could detect one or more properties of the scattered light related to one or more properties of the tissue or other environment. For example, the energy source 224 could emit light having two specified wavelengths related to differences in the absorption spectra of oxygenated and deoxygenated hemoglobin, and the energy sensor 222 could detect a difference in absorption of the two specified wavelengths sufficient to determine a level of oxygenation of blood in the tissue or other environment.

The controller 240 can include an indicator interface module 244 for operating a local indicator 230, a wireless indicator 237, and/or a wired indicator 239. The local indicator 230 can include one or more elements configured to induce a sensation in a wearer of the flexible glove 210 that is related to one or more properties of the tissue or other environment detected using the biosensor 220. The local indicator could include one or more LEDs or other light-emitting elements configured to emit a light that can be sensed by a wearer (e.g., when the wearer is looking at the LED or other light-emitting element). For example, an LED disposed on or near a fingertip on which the biosensor 220 is disposed could emit light having a color, brightness, or other property related to one or more properties of a tissue or other environment proximate to the fingertip. In some examples, the local indicator 230 could include a heat source configured to produce heat that could be sensed by a wearer (e.g., by a finger of the wearer) and that has a property (e.g., a temperature, an energy flux) that is related to one or more properties of a tissue or other environment detected by the biosensor 220. In some examples, the local indicator 230 could include a haptic transducer (e.g., a piezo element, an electroactive polymer, a vibrating element, a solenoid, electrodes configured to inject a stimulating current into skin to cause an electrohaptic stimulus) configured to induce a haptic sensation in a finger or other element of the hand of a wearer and that has a property (e.g., an intensity, a pulse rate) that is related to one or more properties of a tissue or other environment detected by the biosensor 220. The indicator interface module 244 can include controlled current sources, controlled voltage sources, high voltage sources, high voltage switches, DACs, feedback amplifiers, or other elements to operate the local indicator 230 to deliver some stimulus to a wearer related to one or more properties of a tissue or other environment detected by the biosensor 220.

In some embodiments, the local indicator 230 and/or biosensor 220 could include a plurality of indicators and/or biosensors, respectively. For example, the biosensor 220 could include a plurality of force sensors disposed on a fingertip of the flexible glove 210 and the controller 240 could determine a property of tissue in contact with the fingertip (e.g., a compliance of the tissue) and could operate a local indicator 230 disposed in the fingertip to indicate the determined property. In another example, the biosensor 220 could include a plurality of fluorophore detectors (i.e., a plurality of light sources and light sensors configured to illuminate and to receive light emitted from fluorophores in tissue proximate to the light sources and light sensors, respectively) disposed across a fingertip. The local indicator 230 could include a plurality of haptic indicators disposed across the fingertip at locations corresponding to the locations of the fluorophore detectors, and the controller 240 could operate an individual haptic indicator to indicate a property of tissue detected by a corresponding fluorophore detector. Other arrangements and methods of operation of one or more indicators and one or more biosensors are anticipated.

The indicator interface module 244 can also be configured to operate the wireless indicator 237 for sending and/or receiving information about one or more properties of tissue or other environments detected using the biosensor 220. For example, the indicator interface module 244 could be configured to operate the wireless indicator 237 to transmit information to a data acquisition system 270 and/or a wearable display 260. The indicator interface module 244 and/or wireless indicator 237 can optionally include one or more oscillators, mixers, frequency injectors, etc. to modulate and/or demodulate information on a carrier frequency to be transmitted and/or received by an antenna or other radio, microwave, infrared, ultraviolet, ultrasonic, and/or optical emitter/detector. In some examples, the wireless indicator 237 is configured to indicate an output from the biosensor 220 by modulating an impedance of an antenna in a manner that can be detected by the data acquisition system 270 and/or wearable display 260. For example, the wireless indicator 237 can cause variations in the amplitude, phase, and/or frequency of backscatter radiation from the antenna, and such variations can be detected by the data acquisition system 270 and/or wearable display 260.

The indicator interface module 244 can also be configured to operate the wired indicator 239 for sending and/or receiving information about one or more properties of tissue or other environments detected using the biosensor 220. For example, the indicator interface module 244 could be configured to operate the wired indicator 239 to transmit information to the data acquisition system 270, the wearable display 260, or some other remote system using a tether or other physical interconnect (e.g., a cable, one or more wires, a fiber optic element, or combinations of these or other elements, not shown). The wired indicator 239 could include one or more physical connectors configured to allow the connection of a tether, cable, or other means of interconnection. The wired indicator 239 could include level shifters, timers, clock recovery circuits, differential and/or single-ended drivers, oscillator, multiplexers, filters, electrostatic discharge suppressors, or other elements to enable information about one or more properties of tissue or other environments detected using the biosensor 220 to be communicated with some other system using a tether or other physical interconnect. In some embodiments, the wired indicator 239 could include circuitry to power the system 200 (e.g., to power the controller 240) using energy received through a tether or other physical interconnect (for example, from a battery disposed in a watch or similar device worn on a wrist of a wearer of the flexible glove 210 and connected to the wired indicator 239 through a tether or other physical interconnect).

The controller 240 is connected to the biosensor 220 and indicators 230, 237, 239 via interconnects 241, 242, 248, 246, respectively. For example, where the controller 240 includes logic elements implemented in an integrated circuit to form the sensor interface module 243 and/or indicator interface module 244, a patterned conductive material (e.g., gold, platinum, palladium, titanium, copper, aluminum, silver, metals, combinations of these, etc.) and/or wire can connect a terminal on the chip to the biosensor 220 and/or 220 and indicators 230, 237, 239.

It is noted that the block diagram shown in FIG. 2 is described in connection with functional modules for convenience in description. However, embodiments of the system 200 can be arranged with one or more of the functional modules ("sub-systems") implemented in a single chip, integrated circuit, and/or physical feature. For example, while the rectifier/regulator 256 is illustrated in the power supply block 250, the rectifier/regulator 256 can be implemented in a chip that also includes the logic elements of the controller 240 and/or other features of the embedded electronics in the system 200. Thus, the DC supply voltage that is provided to the controller 240 from the power supply 250 can be a supply voltage that is provided on a chip by rectifier and/or regulator components the same chip. That is, the functional blocks in FIG. 1 shown as the power supply block 250 and controller block 240 need not be implemented as separated modules. Moreover, one or more of the functional modules described in FIG. 1 can be implemented by separately packaged chips or other electronic and/or mechatronic elements electrically connected to one another.

Additionally or alternatively, the energy harvesting antenna 252 and an antenna of the wireless indicator 237 can be implemented with the same physical antenna. For example, a loop antenna can both harvest incident radiation for power generation and indicate information via backscatter radiation.

The data acquisition system 270 includes communications interface 274 to send and receive wireless signals to and from the wireless indicator 237. The data acquisition system 270 also includes a computing system with a processor 272 in communication with data storage 276. The data acquisition system 270 can also include user controls, a display, or other elements according to an application. The data storage 276 is a non-transitory computer-readable medium that can include, without limitation, magnetic disks, optical disks, organic memory, and/or any other volatile (e.g. RAM) or non-volatile (e.g. ROM) storage system readable by the processor 272. The data storage 276 can store indications of data, such as indicated sensor readings (e.g., from the biosensor 220), program settings (e.g., to adjust behavior of the controller 240 and/or data acquisition system 270), etc. The data storage 276 can also include program instructions for execution by the processor 272 to cause the data acquisition system 270 to perform processes specified by the program instructions. For example, the program instructions can data acquisition system 270 to perform any of the functions described herein. For example, the program instructions may cause the data acquisition system 270 to provide a user interface that allows for retrieving information communicated from the system 200 (e.g., information about a tissue or other environment generated using the biosensor 220) by displaying that information on a display in response to commands input through the user controls. In some examples, the biosensor 220 could include a camera, and the information indicated to the data acquisition system 270 could include an image detected by the camera, and the display could be operated to show the detected image.

The communication interface 274 of the data acquisition system 270 could additionally be configured to communicate signals to and from a remote system 280. For example, the remote system 280 may be a smart phone, tablet computer, laptop computer, or personal computer, and the communication interface 274 may include a Bluetooth module. In this example, the data acquisition system 270 may be configured to send indicated information collected by the biosensor 220 to the smart phone, tablet computer, laptop computer, or personal computer for storage and offline analysis. In another example, the remote system 270 is a server at a clinic or physician's office or in a surgical suite, the communication interface 274 is a WiFi radio module, and the communication interface 274 communicates through elements of the internet sufficient to enable the transfer of data between the remote server and the WiFi radio module. A physician may use this data to make determinations or diagnoses related to the subject's condition. Further, the data acquisition system 270 may be configured to receive signals from a remote server, such as instructions sent by a physician or surgeon at a remote location to, for example, excise a tissue. Communication interface 274 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The wearable display 260 includes communications interface 264 to send and receive wireless signals to and from the wireless indicator 237. The wearable display 260 also includes a computing system with a processor 262 in communication with a display 266. The wearable display 260 is configured to be worn by a wearer (e.g., a wearer of the flexible glove 210) and to allow the wearer to view images produced by the display 266 that are related to information about the tissue or other environment proximate to the biosensor 220 and indicated by the wireless indicator 237. In some examples, the wearable display 260 is configured to be worn on the head of the wearer such that the display 266 is present within the field of view of the wearer (a "head-mounted display", or HMD). In some examples, the wearable display 260 is configured to be worn on the wrist and/or forearm of the wearer, such that the wearer can view images produced by the display 266 by directing their gaze to their wrist and/or forearm, as appropriate. The wearable display 260 can also include user controls, data storage, or other elements according to an application.

In some examples, the biosensor 220 could include a camera, and the information indicated to the wearable display 260 could include an image detected by the camera, and the display 266 could be operated to show the detected image. The communications interface 264 could be configured to send/receive information from additional systems (not shown). For example, the communications interface 264 could be configured to receive information from surgical imaging systems, information processing systems (for example, a server configured to fuse information from multiple sources, e.g., medical imaging systems, and generate a single composite image or other information including information from the multiple sources), sensors or other elements of a surgical robot, or some other information source. The display 266 could be operated to present such received information to a wearer, in addition to any information indicated by the wireless indicator 237.

Note that the wearable display 260, data acquisition system 270, and/or other components could be connected to the system 200 additionally or alternatively through the wired indicator 239 by being connected through a tether, cable, or other physical connection. In some examples, the wearable display 260, data acquisition system 270, and/or other components could provide power to operate the system 200 (e.g., to power the controller 240) through the wired indicator 239.

IV. Example Processes for Operating a Smart Surgical Glove

Figure 3:
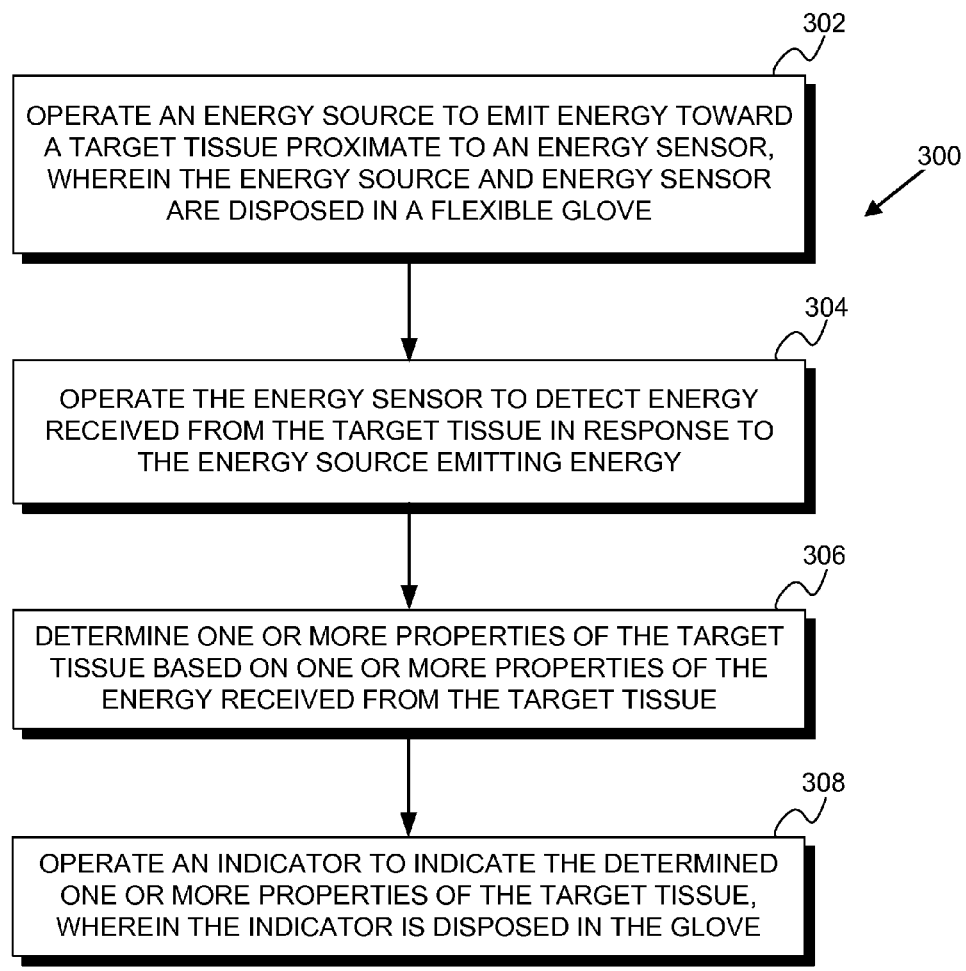
FIG. 3 is a flowchart of an example process for operating a wearable system.

FIG. 3 is a flowchart of a process 300 for operating a biosensor and an indicator disposed on or within a flexible glove. The flexible glove is formed to be mounted on a hand. The biosensor includes an energy source and an energy sensor. The process 300 includes operating the energy source to emit energy toward a target tissue proximate to the energy sensor 302. This could include emitting illumination such that light having one or more properties related to one or more properties of the target tissue is received by the energy sensor. This can include emitting illumination having a specific wavelength or spectral profile, such that the illumination can be absorbed by fluorophores in the environment, emitted by the fluorophores, efficiently transmitted through the environment, or other considerations. In some examples, the fluorophores could be part of an imaging agent in the target tissue. Additionally or alternatively, the wavelength of the emitted light could be specified such that a degree of scattering of the light could be related to one or more properties of the target tissue and such that the degree of scattering of the light could be detected by the energy sensor. Operating the energy source to emit energy toward a target tissue proximate to the energy sensor 302 can include emitting energy having a specified amplitude, wavelength, phase, polarization, ionic content, flux, or other property. Further, operating the energy source to emit energy toward a target tissue proximate to the energy sensor 302 can include emitting energy having different properties at different points in time. For example, it could include emitting energy having a first amplitude, wavelength, polarization, ionic content, flux, or other property at a first point in time and emitting illumination having a second amplitude, wavelength, polarization, ionic content, flux, or other property at a second point in time.

The method 300 additionally includes operating the energy sensor to detect energy received from the target tissue in response to the energy source emitting energy 304. This can include detecting the amplitude, wavelength, degree of polarization, orientation of polarization, location, or other properties of the received energy. It can also include detecting one or more properties of energy received from the target tissue at more than one point in time. For example, the amplitude of light emitted by fluorophores in the target tissue and/or scattered by chromophores or other elements of the target tissue in response to illumination could be detected at a plurality of points in time.

The method 300 additionally includes determining one or more properties of the target tissue based on one or more properties of the energy received from the target tissue 306. This could include determining a concentration of an analyte in the target tissue based on an amplitude, frequency, phase, or other detected property of the energy received from the target tissue. In some examples, this could include determining that the target tissue includes an analyte, for example, cancer cells. This determination could be based on the determination that a determined concentration of another analyte (e.g., a florescent marker configured to selectively interact with cancer cells) was above a specified threshold. Other properties of the target tissue and methods of determining said based on one or more properties of the energy received from the target tissue are anticipated.

The method 300 additionally includes operating an indicator to indicate the determined one or more properties of the target tissue 308 using an indicator disposed in the flexible glove. In some examples, this could include indicating the determined one or more properties to another system (e.g., a computer, a wearable device, a head-mounted display). For example, the indicator could be a wireless transmitter, and operating the indicator to indicate the determined one or more properties 308 could include operating the wireless transmitter to transmit a wireless signal that conveys information related to the one or more properties of the target tissue. In some examples, operating the indicator to indicate the determined one or more properties 308 could include generating a stimulus that can be sensed by a wearer of the flexible glove and that is generated based on the determined one or more properties of the target tissue. For example, the indicator could be operated to generate a resistive element such that the wearer experienced a sensation of heat, and such that the degree of the sensed heat was related to a detected concentration of an analyte. Additional or alternate modes of sensation, methods of inducing said sensation, and relationships between detected properties and induced sensations are anticipated.

Figure 4:
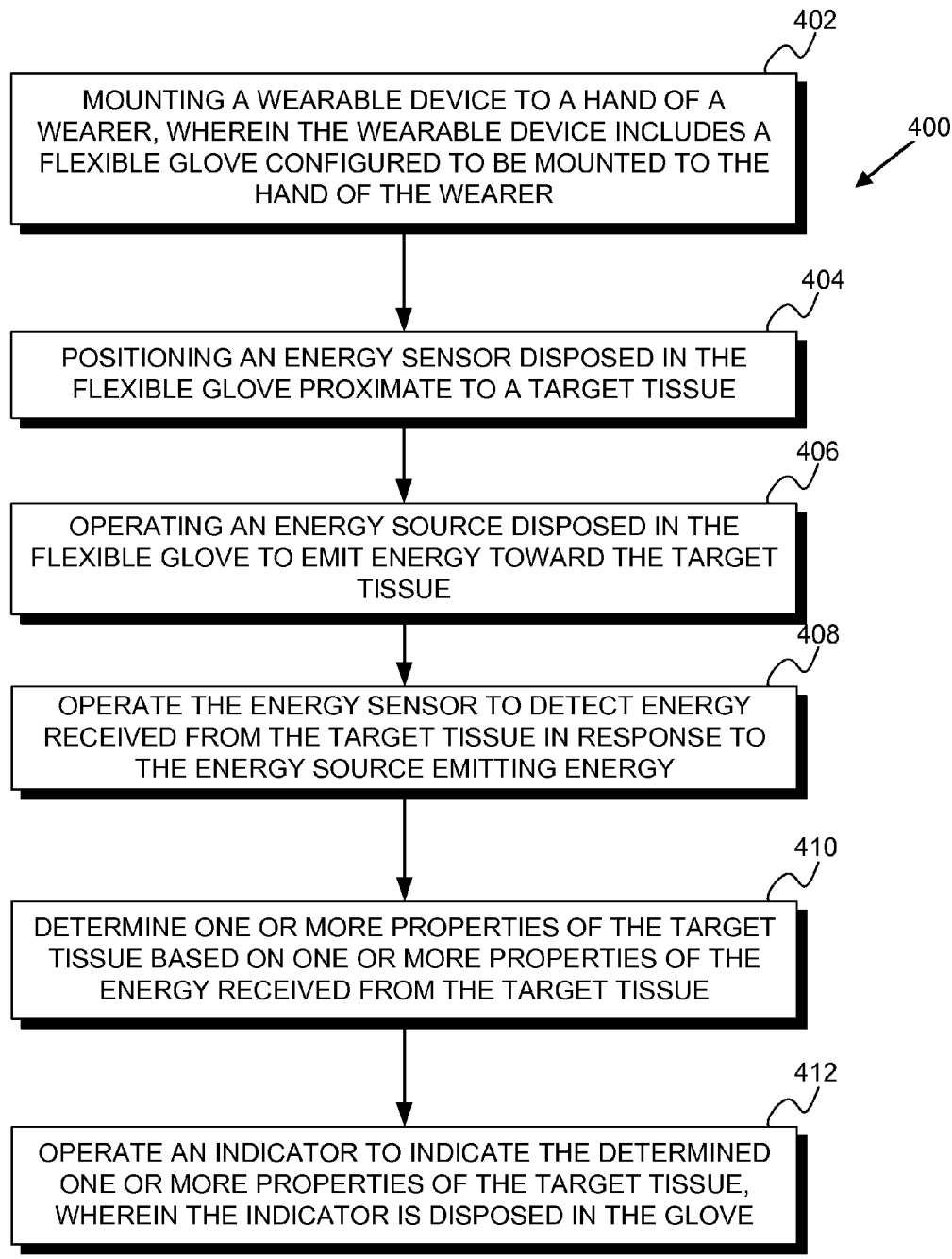
FIG. 4 is a flowchart of an example process for operating a wearable system.

FIG. 4 is a flowchart of a process 400 for using a wearable device to sense one or more properties of a target tissue. The wearable device includes a flexible glove formed to be mounted on a hand. A biosensor and an indicator are disposed on the flexible glove. The biosensor includes an energy source and an energy sensor. The process 400 includes mounting the wearable device to a hand of a wearer 402. This could include donning the glove in a manner such that a sterile condition of the wearable device was substantially preserved. In some embodiments, this could include mounting a first aspect of the wearable device on the hand (e.g., a flexible glove upon which are disposed a biosensor and an indicator) and subsequently mounting a second aspect of the wearable device (e.g., an electronics module containing a controller or other electronic elements) to the first aspect.

The process 400 additionally includes positioning the energy sensor disposed in the flexible glove proximate to the target tissue 404. This could include the wearer moving his or her hand toward the target tissue and extending a finger on which the energy sensor is disposed toward the target tissue. Positioning the energy sensor disposed in the flexible glove proximate to the target tissue 404 could include placing the energy sensor and/or fingertip on which the energy sensor is disposed in physical contact with the target tissue. In some examples, positioning the energy sensor disposed in the flexible glove proximate to the target tissue 404 could include performing a surgical intervention (e.g., creating an incision, dissecting tissues, retracting tissues) to expose the target tissue. In some examples, positioning the energy sensor disposed in the flexible glove proximate to the target tissue 404 could include positioning the energy sensor relative to a marker, tattoo, screw, clip, suture, or other fiducial artifact.

The process 400 additionally includes operating the energy source to emit energy toward the target tissue proximate to the energy sensor 406. This could include emitting illumination such that light having one or more properties related to one or more properties of the target tissue is received by the energy sensor. This can include emitting illumination having a specific wavelength or spectral profile, such that the illumination can be absorbed by fluorophores in the environment, emitted by the fluorophores, efficiently transmitted through the environment, or other considerations. In some examples, the fluorophores could be part of an imaging agent in the target tissue. Additionally or alternatively, the wavelength of the emitted light could be specified such that a degree of scattering of the light could be related to one or more properties of the target tissue and such that the degree of scattering of the light could be detected by the energy sensor. Operating the energy source to emit energy toward the target tissue proximate to the energy sensor 406 can include emitting energy having a specified amplitude, wavelength, phase, polarization, ionic content, flux, or other property. Further, operating the energy source to emit energy toward the target tissue proximate to the energy sensor 406 can include emitting energy having different properties at different points in time. For example, it could include emitting energy having a first amplitude, wavelength, polarization, ionic content, flux, or other property at a first point in time and emitting illumination having a second amplitude, wavelength, polarization, ionic content, flux, or other property at a second point in time.

The method 400 additionally includes operating the energy sensor to detect energy received from the target tissue in response to the energy source emitting energy 408. This can include detecting the amplitude, wavelength, degree of polarization, orientation of polarization, location, or other properties of the received energy. It can also include detecting one or more properties of energy received from the target tissue at more than one point in time. For example, the amplitude of light emitted by fluorophores in the target tissue and/or scattered by chromophores or other elements of the target tissue in response to illumination could be detected at a plurality of points in time.

The method 400 additionally includes determining one or more properties of the target tissue based on one or more properties of the energy received from the target tissue 410. This could include determining a concentration of an analyte in the target tissue based on an amplitude, frequency, phase, or other detected property of the energy received from the target tissue. In some examples, this could include determining that the target tissue includes an analyte, for example, cancer cells. This determination could be based on the determination that a determined concentration of another analyte (e.g., a florescent marker configured to selectively interact with cancer cells) was above a specified threshold. Other properties of the target tissue and methods of determining said based on one or more properties of the energy received from the target tissue are anticipated.

The method 400 additionally includes operating an indicator to indicate the determined one or more properties of the target tissue 412 using an indicator dispose in the flexible glove. In some examples, this could include indicating the determined one or more properties to another system (e.g., a computer, a wearable device, a head-mounted display). For example, the indicator could be a wireless transmitter, and operating the indicator to indicate the determined one or more properties 412 could include operating the wireless transmitter to transmit a wireless signal that conveys information related to the one or more properties of the target tissue. In some examples, operating the indicator to indicate the determined one or more properties 412 could include generating a stimulus that can be sensed by a wearer of the flexible glove and that is generated based on the determined one or more properties of the target tissue. For example, the indicator could be operated to generate a resistive element such that the wearer experienced a sensation of heat, and such that the degree of the sensed heat was related to a detected concentration of an analyte. Additional or alternate modes of sensation, methods of inducing said sensation, and relationships between detected properties and induced sensations are anticipated.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
a glove comprising a plurality of finger portions, wherein the glove comprises a flexible material that substantially prevents passage of microorganisms from the inside of the glove to the outside of the glove through the flexible material;
an energy sensor, wherein the energy sensor is disposed at an end of one of the finger portions and at least partially embedded within the flexible material of the glove, wherein the energy sensor is configured to detect energy received from a target tissue proximate to the energy sensor;
an energy source, wherein the energy source is disposed at an end of one of the finger portions and at least partially embedded within the flexible material of the glove, wherein the energy source is configured to emit energy toward the target tissue proximate to the energy sensor;
an indicator, wherein the indicator is disposed at the end of the one of the finger portions at the end of which the energy sensor is disposed; and
a controller, wherein the controller is disposed in the glove, wherein the controller is configured to:
operate the energy source to emit energy toward the target tissue proximate to the energy sensor,
operate the energy sensor to detect energy received from the target tissue proximate to the energy sensor in response to the energy source emitting energy,
determine one or more properties of the target tissue proximate to the energy sensor based on one or more properties of the energy received from the target tissue proximate to the energy sensor in response to the energy source emitting energy, and
operate the indicator to indicate the determined one or more properties of the target tissue proximate to the energy sensor.

2. The device of claim 1, wherein the energy sensor is a light sensor and wherein the energy emitter is a light emitter.

3. The device of claim 1, wherein the indicator comprises a piezo element.

4. The device of claim 1, wherein the indicator comprises a heat emitter.

5. The device of claim 1, wherein the indicator comprises a haptic transducer.

6. The device of claim 1, further comprising a wireless transmitter, wherein the wireless transmitter is configured to transmit a wireless signal, wherein the wireless signal conveys information related to the determined one or more properties of the target tissue proximate to the energy sensor.

7. The device of claim 1, wherein the energy sensor comprises a camera.

8. The device of claim 1, wherein the energy sensor comprises an infrared light sensor.

9. The device of claim 1, wherein the energy source comprises an infrared light source.

10. The device of claim 1, wherein the energy received from the target tissue proximate to the energy sensor comprises fluorescent light emitted by a fluorophore in the target tissue proximate to the energy sensor, wherein the fluorescent light emitted by the fluorophore is emitted in response to illumination of the target tissue proximate to the energy sensor by light emitted by the energy source, wherein the energy sensor is configured to detect one or more properties of the emitted fluorescent light, wherein the detected one or more properties of the emitted fluorescent light are related to one or more properties of the fluorophore in the target tissue proximate to the light sensor.

11. The device of claim 1, wherein the energy source comprises a light emitter configured to emit light at a specified wavelength toward the target tissue, wherein the specified wavelength is a wavelength of light that is absorbed by hemoglobin, wherein the energy received from the target tissue proximate to the energy sensor comprises a light sensor that is configured to detect light at the specified wavelength that is scattered by the target tissue, wherein the determining one or more properties of the target tissue proximate to the energy sensor comprises determining a level of oxygenation of blood in the target tissue proximate to the energy sensor.

12. A device comprising:
a wireless receiver, wherein the wireless receiver is configured to receive a wireless signal from a wearable device that comprises:
  a glove comprising a plurality of finger portions, wherein the glove comprises a flexible material that substantially prevents passage of microorganisms from the inside of the glove to the outside of the glove through the flexible material;
  an energy sensor, wherein the energy sensor is disposed at an end of one of the finger portions and at least partially embedded within the flexible material of the glove, wherein the energy sensor is configured to detect energy received from a target tissue proximate to the energy sensor;
  an energy source, wherein the energy source is disposed at an end of one of the finger portions and at least partially embedded within the flexible material of the glove, wherein the energy source is configured to emit energy toward the target tissue proximate to the energy sensor;
  an indicator, wherein the indicator is disposed at the end of the one of the finger portions at the end of which the energy sensor is disposed;
  a wireless transmitter, wherein the wireless transmitter is disposed in the glove, wherein the wireless transmitter is configured to transmit a wireless signal to the receiver; and
  a controller, wherein the controller is disposed in the glove, wherein the controller is configured to:
    operate the energy source to emit energy toward the target tissue proximate to the energy sensor,
    operate the energy sensor to detect energy received from the target tissue proximate to the energy sensor in response to the energy source emitting energy,
    determine one or more properties of the target tissue proximate to the energy sensor based on one or more properties of the energy received from the target tissue proximate to the energy sensor in response to the energy source emitting energy,
    operate the indicator to indicate the determined one or more properties of the target tissue proximate to the energy sensor, and
    operate the wireless transceiver to transmit the wireless signal to the receiver, wherein the wireless signal conveys information related to the determined one or more properties of the target tissue proximate to the energy sensor; and
  a further indicator, wherein the further indicator is configured to indicate the determined one or more properties of the target tissue proximate to the energy sensor based on the received wireless signal.

13. The device of claim 12, wherein the further indicator comprises a display, wherein the display is configured to generate a display image, wherein the display image is related to the detected one or more properties of the target tissue proximate to the energy sensor.

14. The device of claim 13, wherein the display is configured to be worn by a wearer of the wearable device.

15. The device of claim 12, wherein the energy sensor of the wearable device comprises a camera, wherein the display image comprises an image detected by the camera.

16. A method comprising:
operating a wearable device on a hand of a wearer, wherein the wearable device comprises:
  a glove comprising a plurality of finger portions, wherein the glove comprises a flexible material that prevents passage of microorganisms from the inside of the glove to the outside of the glove through the flexible material;
  an energy sensor, wherein the energy sensor is disposed at an end of one of the finger portions and at least partially embedded within the flexible material of the glove, wherein the energy sensor is configured to detect energy received from a target tissue proximate to the energy sensor;
  an energy source, wherein the energy source is disposed at the end of one of the finger portions and at least partially embedded within the flexible material of the glove, wherein the energy source is configured to emit energy toward the target tissue proximate to the energy sensor;
  an indicator, wherein the indicator is disposed at the end of the one of the finger portions at the end of which the energy sensor is disposed; and
  a controller, wherein the controller is disposed in the glove, wherein the controller is configured to operate the energy sensor, the energy source, and the indicator, wherein operating the wearable device comprises:
    operating the energy source to emit energy toward a target tissue;
    operating the energy sensor to detect energy received from the target tissue in response to the energy source emitting energy;
    determining one or more properties of the target tissue based on one or more properties of the energy received from the target tissue in response to the energy source emitting energy; and
    operating the indicator to indicate the determined one or more properties of the target tissue.

17. The method of claim 16, wherein operating the indicator comprises using the indicator to generate a haptic stimulus that can be sensed by the wearer, wherein the stimulus is generated based on the determined one or more properties of the target tissue.

18. The method of claim 16, further comprising a wireless transmitter, wherein operating the wearable device further comprises operating the wireless transmitter to transmit a wireless signal, wherein the wireless signal conveys information related to the determined one or more properties of the target tissue.

19. The method of claim 16, further comprising introducing an imaging agent into the target tissue, wherein the imaging agent interacts with a light emitted by the energy source, and wherein the energy received from the target tissue and detected by the energy sensor is a light radiated by the imaging agent in response to interacting with the light emitted by the energy source.

* * * * *